United States Patent [19]
Brownlee et al.

[11] Patent Number: 6,156,306
[45] Date of Patent: *Dec. 5, 2000

[54] PANCREATIC β-CELLS FOR ALLOGENEIC TRANSPLANTATION WITHOUT IMMUNOSUPPRESSION

[75] Inventors: Michael Brownlee, New York; Marshall S. Horwitz, Larchmont; Howard J. Federoff, Rochester; Shimon Efrat, Bronx, all of N.Y.

[73] Assignee: Albert Einstein College of Medicine of Yeshiva University, Bronx, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/732,155

[22] Filed: Oct. 16, 1996

Related U.S. Application Data

[63] Continuation of application No. 08/503,151, Jul. 7, 1995, abandoned, which is a continuation-in-part of application No. 08/382,923, Feb. 3, 1995, abandoned, which is a continuation of application No. 08/292,113, Aug. 17, 1994, abandoned.

[51] Int. Cl.$^7$ .......................... A01N 43/04; A61K 31/70; C12N 15/00; C12N 15/63

[52] U.S. Cl. ..................... 424/93.21; 514/44; 435/320.1; 435/325; 435/69.1; 435/455; 435/456; 536/23.1; 536/23.5

[58] Field of Search ............... 514/44; 424/93.21; 800/2; 435/172.3, 240.2, 240.21, 240.24, 320.1, 325, 69.1, 455, 456; 536/22.1, 23.1, 23.5

[56] References Cited

U.S. PATENT DOCUMENTS 5,139,941  8/1992  Muzyczke et al. ................... 425/172.3

FOREIGN PATENT DOCUMENTS 9302188  2/1993  WIPO .
9320842  10/1993  WIPO .
9416065  7/1994  WIPO .
9416080  7/1994  WIPO .

OTHER PUBLICATIONS von Herrath et al., PNAS, vol. 94, pp. 9808–9813, Sep. 2, 1997.
Efrat et al., PNAS, vol. 92, pp. 6947–6951, Jul. 1995.
Benhamou et al., Diabetes and Metabolism, vol. 24, pp. 215–224, 1998.
Korner et al., PNAS, vol. 89, pp. 11857–11881, Dec. 1992.
Wold et al., Virology, vol. 184, pp. 1–8, Sep. 1991.
Marshall, Science, 269, 1995, 1050–1055.
Miller et al., FASEBJ., 9, 1995, 190–199.
Culver et al., Trends Genetics., 10(5), 1994, 174–178.
Hodgson, Exp. Opin. Ther. Pat., 5(5), 1995, 459–468.
York et al., Cell, 77, 1994, 525–535.
Gooding, Cell, 71, 1992, 5–7.
Pääbo et al., EMBO J., 5(8), 1986, 1921–1927.
Beersma et al., J. Immunol., 151 (9), 1993, 4455–4464.
Geller et al., Proc. Nat. Acad. Sci., 87, 1990, 8950–8954.

*Primary Examiner*—Jasemine Chambers
*Assistant Examiner*—Jill D. Martin
*Attorney, Agent, or Firm*—Amster, Rothstein & Ebenstein

[57] ABSTRACT

The invention provides a cells which express a gene or genes, derived from the adenovirus E3 region, which block allograft rejection. One class of genes blocks the intracellular transport and/or intracellular maturation within the cells of proteins called MHC class I products. Without limitation as to theory, it is believed that blocking the appearance of this class of proteins on the transplanted cell's surface, prevents the host's immune system from rejecting the graft. Another class of proteins acts to permit TNF α-mediated cell cytolysis. In one embodiment, the invention is directed towards engrafting the cells that secrete insulin, which are called alternatively, pancreatic β-cells and islet cells, and thereby provide a treatment of diabetes mellitus.

4 Claims, 5 Drawing Sheets

PANCREATIC β-CELLS FOR ALLOGENEIC TRANSPLANTATION WITHOUT IMMUNOSUPPRESSION

This is a continuation of U.S. application Ser. No. 08/503,151, filed Jul. 17, 1995, now abandoned, which is a continuation-in-part of U.S. application Ser. No. 08/382,923, filed Feb. 3, 1995, now abandoned, which is a continuation of U.S. application Ser. No. 08/292,113, filed Aug. 17, 1994, now abandoned, the contents of all of which are hereby incorporated by reference in their entirety.

1. FIELD OF THE INVENTION

This invention concerns an improvement in the art of the transplantation of tissue for medical purposes. Specifically it concerns methods, vectors and compounds useful in preventing the expression of certain transplantation antigens on the surface of cells to be transplanted. More specifically it concerns the blockage of the cell surface expression of one particular class of proteins the genes for which are located in the major histocompatibility complex (MHC).

2. BACKGROUND OF THE INVENTION

In cases of extreme and life threatening conditions such as renal, liver and cardiac failure, physicians have successfully transplanted tissues between genetically distinct individuals. Even when care is taken to reduce the genetic differences between the host and donor, the recipients of these grafts must usually be given drugs that reduce the activity of their immune system so that the graft is not rejected. Such immuno-suppression entails substantial risks. Even when such immuno-suppression is well tolerated, there are considerable difficulties attendant in minimizing the antigenic differences (matching) between the donor and the recipient that increases the costs and reduces the availability of this mode of therapy. Furthermore, not all tissues can be successfully transplanted between genetically distinct persons.

In principle, for example, diabetes mellitus, one of the most common and, in the longterm, one of the most debilitating chronic diseases, could be "cured" by a successful transplant of the tissue that secrete insulin, the islets of Langerhans. Despite the magnitude of the problem, the availability of islets from cadaveric donors and the successful experience in other situations, e.g., renal, cardiac and hepatic transplantation, there is presently no practical protocol that routinely provides for the survival of histoincompatible islet cells.

The probable causes for this absence may be several. In diabetes mellitus, the disease itself makes immuno-suppression especially hazardous, as diabetics are highly susceptible to infection. Also it appears that some immuno-suppressive agents, e.g., cyclosporine, are directly toxic to islets in high doses and can adversely affect graft survival, while others, e.g., glucocorticoids, are known to increase the subject's insulin requirements and may indirectly jeopardize both the survival and the beneficial effects of the graft. Lastly, in many instances diabetes results from autoimmunity directed toward the islets. To the extent such individuals are immunologically "primed" towards non-allelic islet antigens, their graft rejection would be accelerated. Thus, as an alternative to the present methods of promoting graft survival, which reduce the host's immunity, there is a need in the transplantation art for a method to specifically render the graft invisible to the host's immune system or resistant to its effects.

THE MECHANISM OF GRAFT REJECTION

Except between genetically identical individuals, e.g., identical twins, the cells of each person are recognized by the immune system of others as foreign, i.e., the immune system responds to the graft just as it would respond to a parasite or virus. This so called allograft reaction, unless treated by immune-suppression, leads to the rejection and loss of the graft. The allograft reaction is caused by the recognition of histocompatibility antigens on the surface of the cells of the graft by the lymphocytes of the recipient individual. With rare exceptions, e.g., the ABO blood groups in transfusions, the host lymphocytes of greatest importance to an allograft reaction are of the type that recognize antigen directly on cell surfaces, so-called thymic lymphocytes (T-lymphocytes).

From the fact that only grafts between genetically identical individuals are truly stable, one may conclude that almost any protein can become a histocompatibility antigen when the host's and recipient's genes encoding it are different. This surmise has been experimentally verified. However, the rapidity with which an allograft is rejected varies greatly depending upon the nature of the histoincompatibility between the host and graft. In particular, every species of higher vertebrates contains a closely linked complex of multiple genes at which genetic differences are found to cause the most rapid and severe allograft reactions. This complex of genes is called the Major Histocompatibility Complex (MHC) of the species. Several types of proteins are encoded within the MHC, including two classes of cell surface proteins, conventionally called class I and class II MHC products. In humans the class I products are also referred to as HLA-A, HLA-B and HLA-C, and the class II products are termed HLA-DR. Many cell types, such as β-cells, express only MHC class 1 products.

Class I and class II MHC products are not only histocompatibility antigens, they are also central to antigen recognition by T-lymphocytes. Although the different T-lymphocytes from an individual can recognize and distinguish among perhaps millions of potential antigens, each of that individuals T-lymphocytes can recognize its particular antigen only when the antigen is either an MHC class I or class II product or is physically complexed with one. These observations suggest that the life of an allograft could be extended indefinitely were some mechanism available to prevent the expression of MHC products altogether by the graft.

THE VIRAL PRODUCTS THAT OVERCOME HOST IMMUNITY

The problem of avoiding a host's immune reaction is of interest not only to transplant surgeons but also to parasites such as viruses. Viruses, of course, are able to reproduce only within a viable cell of the infected host. Viruses frequently kill the infected cell when they redirect the cellular machinery towards the production of viral particles (virions). Surprisingly then, one of the major host defenses against viruses are cytotoxic T-lymphocytes (CTL) which kill the infected cells. The host apparently prevents, to some significant degree, the further release of virions by killing the infected cell when viral antigens can be detected. In response, certain viruses have evolved mechanisms to reduce or avoid the host's immune attack on the host's cells in which the virus is replicating (reviewed, Gooding, L. R., 1992, CELL 71:5–7) by blocking the presentation of newly synthesized antigens. Some of these mechanisms apparently specifically prevent the maturation of MHC class I products onto the cell surface. Because the complex of MHC product and antigen is formed as the product matures, the display of newly synthesized viral antigens is blocked.

Researchers have recognized that adenovirus infected cells are poorly recognized and lysed by CTL. To determine which viral products are particularly involved, the isolated E3 region of adenovirus was co-transfected, along with a selectable marker, into the 293 embryonic kidney cell line, which had been transformed with adenovirus and contained adenovirus early genes products, that rendered the adenovirus E3 promoter active.

Stable transfectants were isolated by selection of the marker gene and a single clone expressing high levels of gp19 was selected for further study. This transfected clone was found to have undergone an about 5–10 fold reduction in the amount of HLA-A and somewhat smaller reduction in total MHC class 1 products. There were no studies of the functional consequences of this reduction. Burgert, H-G & Kvist, S., 1985, CELL 41:987–97.

Subsequently, these authors introduced a murine MHC class I product ($K^d$) into the selected clone and showed that this clone was resistant to $K^d$-specific CTL, Burgert, H-G, 1987, PROC.NATL.ACAD.SCI. 84:1356–60. Studies of murine immune responses to adenovirus antigens, using varying deletion mutants spanning the E3 region and anti-MHC monoclonal antibodies, establish that the gp19 protein (gp19) both binds murine MHC product and is necessary and sufficient for the inhibition of its expression on the surface of the embryonic kidney cell. Burgert, H-G., & Kvist, S., 1987, EMBO J. 6:2019–26; Rawle, F. G. et al., 1989, J.IMUUHOL. 143:2031; Cox J. H., et al., 1991, J.EXP.MED. 174:1629–37; Hermiston, T. W. et al., 1993, J. VIROLOGY 67:5289.

The issue whether the inhibition by gp19 of the expression of MHC class I products is a general effect, or one specific to adenovirus transformed cell lines remains incompletely resolved. The expression of gp19 in cells other than the embryonic kidney line of Burgert is associated with the inhibition of glycosylation of MHC class 1 heavy chain indicating that this molecule does not exit the endoplasmic reticulum, Burgert, 1985, supra.; these or other processes block the presention of viral antigens in acutely infected cells, Cox, J. H., et al., 1990, SCIENCE 247:715–718. However, there was no evidence of a reduction in the total amount of cell surface MHC class I product other than in the adenovirus-transformed cell lines studied by Burgert. Routes, J. M., & Cook, J. L., 1990, J.IMMUNOL. 144:2763.

The scientific literature does not establish whether the chronic presence of gp19, in quantities attainable by present methods without cytotoxic effects, will render a cell resistant to CTL. CTL are fully active against targets that have between 0.1%–0.2% of the normal concentration of MHC class I products. Vitiello, A., et al., 1990, SCIENCE 250:1423. Thus, the relative reduction in MHC class I expression needed to prevent CTL activity is approximately 100 fold greater than that observed in the most strongly inhibited example of Burgert. Thus, while the evidence is strong that gp19 causes an acute failure of adenovirus infected cells to present newly synthesized antigens and blocks the cell-surface-display of newly synthesized MHC molecules, it does not indicate whether gp19 will be sufficient to permanently eliminate a sufficiently large fraction of MHC class I products from the surface of cells expressing gp19 to render the cells resistant to the effects of CTL.

Other proteins that can be used to inhibit the expression of newly synthesized MHC class I products can be found. A herpes simplex virus (HSV) virus protein, ICP-47, having similar properties to adenovirus gp19 has been described. York, I. A., et al., 1994, CELL 77:525–35. Human cytomegalovirus appears also to express a protein having this activity. Beersma, M. F. C., et al., 1993, J. IMMUNOL. 151:4455–64.

TREATMENT OF DIABETES MELLITUS BY TRANSPLANTATION OF B-CELLS

Diabetes mellitus is a disease of glucose regulation characterized by excessive blood glucose caused by either an absolute deficiency of insulin-secreting β-cells or, more commonly, by a combination of hyporesponsive β-cells and the resistance of the subject to the effects of insulin. Although there is extensive clinical evidence that insulin therapy combined with strict adherence to dietary control, can control the acute effects of diabetes such as ketoacidosis, such therapy does not stabilize the blood glucose levels sufficiently to prevent the long term ophthalmologic, neuropathic, nephropathic and arterial complications of the disease.

To prevent these complications, physicians have experimented with the transplantation of islets obtained from the pancreas of human cadaveric donors. These reports demonstrate the practicability of techniques to obtain and isolate islets from cadaveric donors and to implant the islets into the liver of diabetic subjects by injection of isolated whole islets into the portal circulation. Scharp, D. W., et al., 1990, DIABETES 39:515–8. The results of a series of longitudinal studies of several patients, however, show that, at levels of immuno-suppression appropriate for renal or hepatic allografts, islet cell transplants do not routinely survive and function well enough to eliminate the need for exogenous insulin. Ricordi, C., 1992, TRANSPLANTATION 53:407–414. Among the explanations available for this phenomenon is that many diabetic patients have developed an auto-immunity to islet cells, a so-called insulinitis, which may cause an unusually intense allograft reaction to the transplanted islets. Alternatively, the cyclosporine appears to have a direct toxicity for β-cells and glucocorticoids have known diabetogenic effects that antagonize insulin and jeopardize graft function and survival. Whatever the mechanism, the results of these studies show that conventional immuno-suppression is generally not successful in enabling islet transplantation. Thus, there is an unmet need in medical practice, for a method to transplant islet cells between histoincompatible individuals.

There have been attempts to answer the question whether the complete suppression of MHC class I products from the surface of the β-cells would allow indefinite survival of allograft islets without immuno-suppression, in murine experimental systems. These studies employ transgenic animals lacking both maternal and paternal copies of the $β_2$-microglobulin gene, the gene necessary for the expression of functional MHC class 1 products. These studies show that islet grafts of normal recipients from $β_2$-microglobulin deficient donors, frequently, though not invariably, survive for an indefinite period. Orsorio, R. W., et al., 1993, DIABETES 42:1520–27; Markman, J. F., et al., 1992, TRANSPLANTATION 54:1085–89. However, when such islets were transplanted into NOD mice, which spontaneously develop an autoimmune diabetes and are considered to be a model for human type 1 diabetes, there was no prolongation of the survival of the grafted islets. Markman, supra. The failure of $β_2$-microglobulin deficient islets to survive in NOD mice does not imply that MHC-class 1 restricted CTL are not essential to the development of diabetes in the NOD model. Experiments show that $β_2$-microglobulin deficient-NOD mice, which show markedly reduced levels of MHC class I products in all tissues do not develop either diabetes or the lymphocytic infiltrate of their islets, a condition which is called insulinitis. Serreze, D. V., et al., Mar. 1994, DIABETES 43:505–9; Wicker, L. S., et al., Mar 1994, DIABETES 43:500–4. Together these results establish that, at least in mice, the removal of MHC class I products from the surface of islets by means of deletion of the $\beta_2$-microglobulin gene of the islets does not lead to a successful therapy in a mouse having a CTL dependent auto-immune diabetes.

To meet the need for an effective method to prevent the rejection of islet grafts, some have proposed the use of "masking" agents, such as F(ab')$_2$ anti-HLA antibodies to prevent recognition by the CTL of the MHC class I product. Data indicate that the pre-treatment of human islets with anti-HLA antibody effectively prolongs the survival of transplants into the renal-subcapsular space of murine hosts to as much as 200 days; while absent such pretreatment rejection occurs within 7 days. U.S. Pat. No. 5,283,058 to D. Faustman. The examples presented by Faustman concern xenografts, particularly the engraftment of mice with human islets. No data are presented by Faustman showing that this method would be effective in preventing allo-rejection, i.e., the rejection of murine islets by mice. Because xenograft rejection is most often of the hyperacute type mediated by preformed antibodies, the projection of the reported results concerning the Faustman technique to the case of allotransplantation is of uncertain outcome. Faustman also suggests that unspecified viral proteins may be used in conjunction with, or as an alternative to, the use of masking agents to decrease MHC class I expression to prolong islet graft survival.

SUMMARY OF THE INVENTION

The invention provides a method and vectors to express a gene, derived from a virus, that blocks the intracellular transport and/or intracellular maturation within the graft of proteins called MHC class I products. Without limitation as to theory, it is believed that blocking the appearance of this class of proteins on the transplanted cell's surface, prevents the host's immune system from rejecting the graft. In one embodiment, the invention is directed towards engrafting the cells that secrete insulin, which are called alternatively, pancreatic β-cells and islet cells, and thereby provide a treatment of diabetes mellitus.

The present invention provides a method of rendering cells more readily transplantable between histoincompatible individuals; the pancreatic islet is a non-limiting example of one such type of graft. The method comprises obtaining a population of cells to be transplanted, e.g., by explantation from a cadaveric donor, and introducing into substantially all of the cells of the population a vector that makes a nucleic acid product.

In one embodiment the vector acts by producing a protein expression product that prevents the expression of the MHC class I products. In another embodiment, the vector may act by producing protein products which inhibit a variety of host immune responses important in graft rejection. In an alternative embodiment the vector may act by producing a nucleic acid expression product having a specific nucleic acid that interferes with the production of the MHC class I products.

Any population of cells suitable for beneficial implantation into a subject may be employed. Suitable cells are preferably stable and non-transformed. Stable, non-transformed cells are cells having a life-span that is at least several weeks and most preferably many months or years and are cells with normal growth characteristics such that upon transplantation into an immunodeficient host, such as a nude mouse, there is no tumor formed.

Proteins suitable for the practice of the invention can be found among human virus proteins; adenovirus (Ad) gp19 and HSV ICP-47 are representative non-limiting examples. The invention further provides for vectors to express MHC class I inhibitory proteins in the population to be transplanted. Expression vectors suited for the present invention necessarily must be able to successfully transfect substantially all the cells, which is preferably more than half of the cells, more preferably greater than 80% of the cells, and most preferably greater than 95% of the cells. Such vectors must not produce other cytopathic effects that would interfere with other normal functions of the cells to be transplanted. Suitable examples of such vectors include replication defective virus vectors based on HSV and adenovirus, and vectors based on the satellite virus, adeno-associated virus (AAV). The invention further provides populations of non-transformed cells, i.e., cells whose growth is controllable, that lack detectable quantities of MHC class I products on their surface as determined by their ability to be targets of lysis by T-lymphocytes of the appropriate specificity.

DETAILED DESCRIPTION OF THE INVENTION

The present invention is based, in part, on the unexpected results obtained with transgenic mice that had incorporated into their genome a copy of the Ad E3 region under the control of a rat insulin promoter. The E3 transcription unit encodes for the proteins p14.7, p10.4/14.5 as well as gp19. These transgenic animals are not generally depleted of MHC class I products since the rat insulin promoter is not active in most cell types, i.e., it is not a constitutive promoter, but rather is active only in islet cells. Islets from these transgenic animals were transplanted into animals having both the MHC and background incompatibilities. These results demonstrate for the first time in an in vivo situation that products of the Ad E3 genes, including gp19, which downregulates expression of cell-surface MHC class I, and the 14.7 protein and the 10.4/14.5 protein complex, which inhibit cytolysis by tissue necrosis factor (TNF) α a are capable of preventing allograft rejection. In contrast to the results of Orsorio, R. W, et.al. and Markman, J. F. et. al. supra, who used a murine embryonic stem cell and gene knock out techniques which are currently only applicable in mouse strains, the technique of adenovirus E3 gene insertion of the present invention is potentially applicable in any species including humans.

PROTEIN PRODUCTS OF THE ADENOVIRUS EARLY TRANSCRIPTION REGION 3 INHIBIT HOST IMMUNE RESPONSES IMPORTANT IN GRAFT REJECTION

The adenovirus (Ad) early transcription region 3 (E3) is 3.5 kilobases in length and encodes gp19, p14.7, p10.4/14.5 and at least 3 other polypeptides. Two open reading frames which could code for other, as yet unobserved proteins, are also present. The products of the E3 region are known to inhibit a variety of host immune responses which are potentially of great importance in the mechanism of host rejection of foreign tissue.

In addition to the effect of gp19 on the expression of class 1 MHC products which is discussed in greater detail below, the 14.7 protein and the 10.4/14.5 protein complex, for example, are known to inhibit tumor necrosis factor (TNF) α-mediated cytolysis of Ad-infected cells (Wold, W. S. M. and Gooding, L. R., 1991 VIROLOGY 184:1–8; Gooding, L. R. and Wold, W. S. M., 1990 CRC IMMUNOLOGY 10:53–70). The isolated 14.7 protein has been shown to antagonize the antiviral effects of TNF in a vaccinia model system (Tufariello, J., et.al., 1994 JOURNAL OF VIROLOGY 68:453–462).

The prolonged survival of transplanted tissue in which the entire Ad E3 region is expressed will be discussed in greater detail below. The prolonged survival of such tissue upon transplantation may be due to the inhibitory effects of the E3 proteins on different pathways of the host immune response important to rejection.

ISOLATION OF A NUCLEIC ACID ENCODING A PROTEIN INHIBITOR OF THE CELL SURFACE EXPRESSION OF MHC CLASS I PRODUCTS

Medical scientists concerned with the pathogenesis and pathobiology of viral infection have identified human viruses that reduce the concentration of MHC class I products on the surface of infected cells or are otherwise resistant to lysis by antigen specific cytotoxic T-lymphocytes. See § 2.2 supra. In two cases, Ad gp19 and HSV ICP-47, the proteins chiefly responsible for the phenomenon (hereinafter "MHC blocker proteins") have been identified by techniques familiar to those skilled in the art. Such techniques include immunoprecipitation with antisera specific for the MHC product, in which case the operative viral protein is co-precipitated after infection of cultured cells with viruses having various non-lethal deletions to determine which viral gene is necessary for the reduction of MHC class I products.

Once the appropriate viral gene is identified, it can most readily be cloned into an expression vector by PCR amplification wherein the PCR primers have incorporated suitable restriction sites so that the amplified product may be directly ligated into a cloning or expression vector. These techniques are further exemplified in the section below wherein the cloning and insertion of gp19 into a herpes amplicon vector to make pHSVgp19 is demonstrated. The cloning of the ICP47 gene by the same technique is described in Banks T. A., et al., 1994, Virology 200:236–245.

CONSTRUCTION OF VIRAL VECTORS

The present invention is intended to encompass the production of MHC blocker proteins by any effective means that is not cytopathic, i.e, does not interfere with the cells processes except for the expression of MHC class I products, and is effective in the majority of the cells of a treated population. Such means include replication defective viral vectors. Replication defective viral vectors may be derived from competent pathogenic viruses or may be derived from natural replication-defective satellite or passenger virus, i.e., virus that has developed an obligatory reliance on the assistance of another virus for replication.

A replication defective viral vector plasmid contains minimally 5 elements: 1) a prokaryotic origin of replication and selectable gene for propagation in a prokaryotic host, e.g., in E. coli; 2) a viral origin of replication; 3) a viral packaging sequence so that the nucleic acid of the vector plasmid can be packaged into virus particles or virions; 4) a promoter that is active in the target cell population with a polyadenylation signal and 5) a multiple cloning site for the insertion of the nucleic acid encoding a gene of interest.

A non-limiting example of a replication defective virus is a herpes amplicon vector, in which the viral origin of replication and packaging sequences are derived from herpes virus. The herpes amplicon vector contains no herpes virus structural proteins, which are supplied by a co-infecting helper virus. However, the advantages of using a replication defective vector would be lost if a viable herpes virus was used as a helper virus. Therefore, the helper virus is also made replication defective, except when grown on a complementing cell line.

A productive infection by herpes virus requires the presence of a functional herpes Immediate Early 3 (IE3) gene. The amplicon vectors can be produced through the use of a replication defective "helper" herpes virus lacking an IE3 gene and a "packaging line" which has had a copy of IE3 inserted into its genome. The techniques for the production of herpes amplicon vectors have been described elsewhere. Geller, A. I., et al., 1990, PROC.NATL.ACAD.SCI. 87:8950; Geller et al., WO92/07945 and WO 90/09441 which are herewith incorporated by reference in their entirety. The production of "packaging lines" has been described elsewhere. Johnson, P., et al., 1992, J.VIROL. 66:2952–65.

Herpes amplicon vector virions can be produced as follows: a packaging line is transfected, using for example Lipofectin®, with a vector plasmid; approximately 20 hours later the cells are infected with the helper virus. The helper virus and packaging cell line contain all the genes necessary to replicate the plasmid DNA and package it in a herpes virion. Because the vector plasmid is typically much smaller than the herpes virus itself (10–15 Kb v. 150 Kb) the vector plasmid contains a much higher density of replication origins than does the helper virus. Due to the higher density of replication origins, vector plasmid containing virions predominates. Each virion will also contain multiple concatenated copies of the vector plasmid so that each will contain about 150 Kb of DNA.

The presently available helper virus and packaging cell lines give rise to recombinant, replication competent viruses at a rate of about $1/10^6$ virions. This rate may be further reduced by reducing the length of the regions of homology between the helper virus and the IE3 insert in the packaging cell line. A still further reduction in the rate of recombinant replication competent viruses can be obtained with helper viruses having more than one necessary gene deleted and amplified in corresponding multigenic-complementing packaging lines, in which the complementing genes are unlinked.

The promoter of the transcription of the MHC blocker protein gene can be any promoter that is active in the cell population of interest. The herpes promoter IE 4/5, that has been used in the working examples below, is a non-limiting example. Other potent, constitutive promoters suitable for the practice of the invention include the cytomegalovirus-1 promoter and the Rous sarcoma virus long terminal repeat (LTR). A strong promoter that is specifically active in the cell population of interest can also be employed, e.g., an insulin promoter may be used for the expression of the MHC blocker gene in pancreatic β-cells.

An alternative to the herpes amplicon vector is a replication defective viral vector based on adenovirus. The construction of these vectors is described in the following: Davidson, B., et al., 1993, NATURE GENET. 3:219; LeGal LeSalle, et al., 1993, SCIENCE 259:988; Haddada, H., et al., 1993, Bioch. Biophy. Res. Com. 195:1174–83; Rosenfeld, M. A. et al., 1992, CELL 68:143–155 and patent publications WO 94/08026 by Kahn, A., et al., and WO 9410322 by Herz, J., et al. (each of which is herewith incorporated by reference). Typically, adenovirus vectors are produced in the HEK-293 cell line containing the complementing E1A and E1B genes.

The third type of replication deficient viral vector is based upon naturally occurring satellite or passenger viruses, for example, Adeno-associated virus (AAV), which despite its name, can utilize either herpes or adenovirus as a helper virus. An advantage of AAV is that the viral stocks may be freed of helper virus by simply heating the viral stock to 56° C. for two hours to which AAV is resistant but the enveloped herpes virus and adenovirus are not. A second potential advantage of AAV is that, in contrast to the adenovirus and herpes virus vectors, AAV vectors are integrated in the host chromosome, so that the gene encoding the MHC blocker is not diluted by graft cell turnover. The construction and use of AAV vectors is described in U.S. Pat. No. 5,139,941 to N. Muzyczka et al., which is herewith incorporated by reference.

For the practice of the present invention it is important that the transfection of the MHC blocker expression vector does not lead to a productive viral infection because this might cause the death of the infected cells. For this reason replication defective vectors are most suitable. In contrast, the productive infections of naturally occurring herpes or adenoviruses cause cytotoxicity thereby making the cells unsuitable for the practice of the invention. Transplantation of productively infected cells would, of course, also be unsuitable because the transplantation would cause an infection in the host as well.

The choice of the vector is determined by the characteristics of the population of cells to be transfected. The use of vectors, such as adenovirus and herpes virus based vectors, that do not integrate into the genome is compatible with cells having minimal mitotic activity in vivo, such as islet β cells. Cells that are normally more active mitotically are more suited to use of a vector that integrates such as the AAV vector.

TRANSFECTION OF CELLS AND DETERMINATION OF THE RESULTS

The population of cells to be transfected with an MHC blocker expression vector of the invention may be obtained by any technique that yields a population of cells that can be sustained in a metabolically active state in tissue culture between 24 and 72 hours; this being the time needed to reduce MHC class I products from the surface of the transfected cells relative to normal cells. As used herein, "normal cells" refers to cell populations which have not been transfected with the MHC blocker expression vector.

In a non-limiting example the cells can be neuron precursors or a neuronal stem cell line which differentiates upon transplantation. The culture conditions appropriate for these cell types are reported by Reynolds, B. A. & Weiss, S., 1992 SCIENCE 255:1707–10 and Renfranz, P. J., et al., 1991, CELL 66:713–729. Neuronal transplantation can be useful in the treatment of degenerative neurological diseases as for example Parkinson's Disease and Alzheimer's Disease.

In a further non-limiting example, islets from a human cadaveric pancreas can be isolated by techniques, well known to those in the art. Briefly, after removal from the cadaver donor, a pancreas is perfused with a transport solution and may be stored at 4° C. up to 12 hours while in transit. Isolation of the islets is begun by retrograde infusion through the pancreatic duct of a collagenase solution. The pancreas is then placed in a recirculating, temperature controlled islet separating reaction chamber. The collagenase digestion continues for between 20–30 minutes during which time the tissue reaction mixture is perfused from below, at a controlled rate, such that the smaller islets are separated upwards from the more rapidly sedimenting larger debris of the exocrine pancreas. The islet preparation is further purified by centrifugation over a step density gradient. Ricordi, C., et al., 1990, Surgery 107:688; Ricordi, C., et al., 1988, Diabetes 37:413. The islets are recovered as intact organoids having diameters of about 150 μm. The number of islet cells in an islet preparation can be estimated with accuracy by disaggregating the islets with trypsin and staining with dithizone.

Following their isolation the islets can be cultured in hepes buffered CMRL medium supplemented with 10% Fetal Calf Serum, 2 mM glutamine and antibiotics at a concentration of $10^6$ cells/ml. The cells can then be exposed to the MHC blocker expression vector. Effective expression can be obtained with a multiplicity of infection (MOI) of about 1–5 when herpes virus vectors are to be used and an MOI of between $10^2-10^3$ when adenovirus vectors are employed.

After a period of incubation of between 1–3 days the transfected islet cells should be assayed to determine the amount, if any, of MHC class I product on the cell surface and implanted. In a preferred embodiment, the amount of cell surface MHC class I products are immunologically undetectable as a result of transfection. Those skilled in the art will understand that some experimentation may be useful to determine the promoter and vector combination which provides the highest levels of mRNA encoding the blocking protein. Assays to determine the extent of remaining MHC class I on the cell surface can be of three types, the choice of which is determined by the type of cell which is to be transplanted and the circumstances of the procedure. Immunohistochemical techniques in combination with flow cytometry can be used to quickly determine the level of cell surface expression. However, for certain cell types, e.g., islet cells, the normal levels of MHC expression are below that easily detectable by this technique. For these cells the level of expression may be increased by culture of the cells with γ-interferon, which stimulates the expression of MHC class I products. This technique allows normal islet cells to be readily distinguished from those in which the MHC blocker vector has been successfully introduced.

A second technique whereby cell surface MHC class I can be detected is by use of a cytotoxic T-cell (CTL) that are specific for the particular MHC class I product present on the target-test population. CTL are fully active against targets that have between 0.1%–0.2% of the normal concentration of MHC class I products. Vitiello, A., et al., 1990, SCIENCE 250:1423. Thus, the ability of primed CTL clones to lyse targets from the MHC blocked cell population is a sensitive test of the efficacy of the blockage of MHC class I product.

A final technique that can be used to determine the efficacy of the present invention is to determine the survival of experimental grafts. The foregoing theories and models are provided to assist in the practice of the invention. The invention, however, is not limited by the foregoing models, but is intended to encompass any technique of allowing for the survival of histoincompatible grafts in immunocompetent hosts by causing the expression of a protein that alters or modifies the expression of MHC class I products so as to prevent graft rejection.

Thus, the survival of an MHC class I histoincompatible graft, treated by the method of the invention, for greater than 3 months in a person or animal that is not receiving any immuno-suppressive drugs or has an otherwise compromised immune system is considered evidence that there is no immunologically detectable MHC class I products expressed on the cell surface of the graft. As used herein, the reduction of the MHC class I products to below 0.2% of the normal level determined by immunofluorescence is also considered to be "immunologically undetectable" as is a reduction in the susceptibility of the cells to lysis in vitro by CTL so that the antigen specific lysis is reduced by more than a factor of ten and most preferably by more than a factor of one hundred.

As used herein, however, MHC class I products are not considered to be "immunologically undetectable" when normally expressed, cell surface MHC class I products of a cell have been complexed, while on the cell surface, with a ligand that is not produced by the cell. Although the binding of such blocking or masking ligands to MHC class I products may interfere with an assay for MHC class 1 products, the products, nevertheless, could be detected indirectly by use of the appropriately labeled masking ligands or by secondary labels specific for the masking ligand.

The implantation of the cell population of interest following the exposure of the cells to the expression vector of the invention may be performed by any technique recognized in the art for the implantation of tissues. Non-limiting examples include the perfusion of pancreatic islets into the portal circulation by cannulation of the umbilical vein and the implantation of pancreatic islets under the capsule of the kidney. The quantity of cells to be engrafted can be determined by routine experimentation and consideration of the subjects pre-engraftment insulin requirements. Successive engraftments to augment the dose of cells can be employed, if the subject continues to require insulin therapy.

ANTISENSE VECTORS

In an alternative embodiment of the invention the MHC class I blocking effect of the vector can be mediated by an antisense nucleic acid which is synthesized by the vector. The antisense nucleic acid can be a nucleic acid complementary to the mRNA that encodes the MHC class I products. However, because humans have multiple MHC class I encoding genes and because of the polymorphism of these genes, a single antisense message would not be ideally suited to prevent the expression of each of the alleles. In an alternative, preferred embodiment, the vector can be selected to encode an antisense nucleic acid that is complementary to a non-polymorphic protein that is necessary to express MHC class I products on a cell's surface. One such protein is the transporter associated with antigen processing (TAP). See, e.g., Momburg, F., et al., 1994, NATURE 367:648–51. The sequence of the region which encodes the human TAP has been determined. Beck, S. et al., 1992, J.MOL.BIOL. 228:433–41 (which is herewith incorporated by reference). An antisense vector that prevents the synthesis of the tap1 or tap2 proteins can be used to prevent MHC class I expression according to the invention.

The present invention is described in the following Experimental Details Section which is set forth to aid in the understanding of the invention, and should not be construed to limit in any way the invention as defined in the claims which follow thereafter.

EXPERIMENTAL DETAILS SECTION

GENERATION OF TRANSGENIC MICE CONTAINING THE ADENOVIRUS E3 REGION

Figure 1:
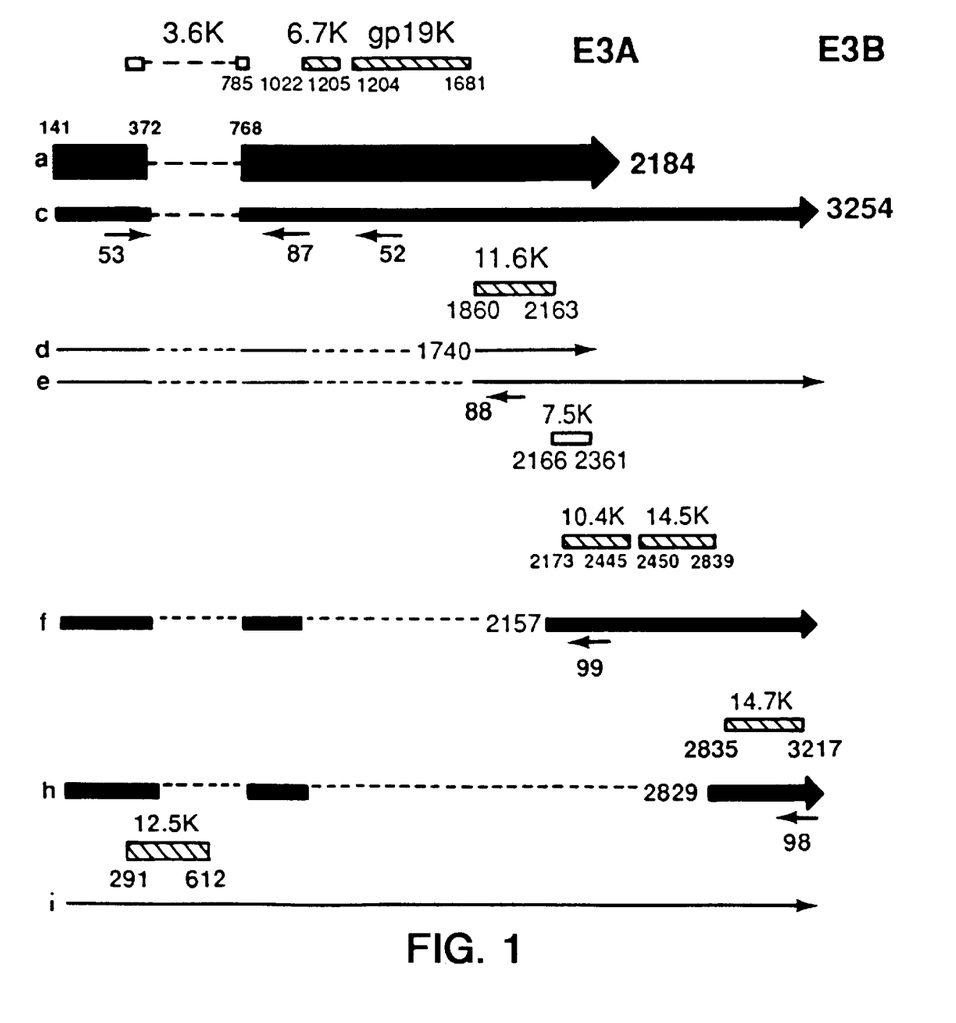
FIG. 1 depicts an E3 transcription map and open reading frames (ORFs). Exons are designated by solid arrows, interrupted by dashed lines representing introns. The line thickness represents the relative amounts of Ad mRNAs (a–i) as determined from productive Ad2 infection of KB cells. The short arrowheads represent oligonucleotides used in PCR reactions. The hatched rectangles represent identified proteins, while the stippled rectangles represent putative translational products not yet identified. The coordinates of the mRNAs and proteins are shown in relationship to the E3 transcriptional start site in infected cells. Adenovirus genomic bp 27611 is equivalent to the first base of the E3 transcript. E3A and E3B designate the two polyadenylation signals.

A fragment of Ad2 genomic DNA extending from the BspEI site at nucleotide 27752 to the NdeI site at nucleotide 31076 was placed under control of the rat insulin II promoter between the XbaI and SalI sites in the pRIP-Tag plasmid (Hanahan, D., 1985, NATURE 315:115–122), by converting the 5' and 3' ends to NheI and SalI linkers, respectively. In the resulting construct, the SV40 Tag sequence is excised and replaced with the Ad E3 genomic DNA fragment which contains the native splice sites and polyadenylation signals of the E3 genes (FIG. 1) (Duerksen-Hughes, P. J., et al., 1993, J. VIROL. 65(3):1236–1244; Fejer, G., et al., 1994, J. VIROL. 68:5871–5881).

The new plasmid DNA was linearized with Sal1 and microinjected into B6D2/F1 (C57BL/6×DBA/2/F1) 1-cell embryos. Eight founder RIP-E3 animals were generated. Of these founder animals, lineage #7, containing approximately 35 copies of the transgene and expressing the highest amount of mRNA for gp19, was studied in detail. Transgenic mice were identified by Southern blotting analysis of tail DNA.

TRANSPLANTATION OF PANCREATIC ISLETS INTO ALLOGENIC RECIPIENTS

The RIP-E3 B6D2/F2 transgenic founder was backcrossed with C57BL/6 mice and bred to homozygocity at the RIP-E3 locus. A homozygous RIP-E3 H-$2^b$ male was mated with a BALB/c female. The presence of the H-$2^{b/d}$ haplotype in the progeny was confirmed by PCR analysis utilizing restriction endonuclease polymorphism based on published sequences for $K^b$ and $K^d$ (Weiss, E., et al., 1983, *EMBO* 2:453–462). These mice served as islet donors. Islets were isolated by collagenase infusion of the pancreas through the common bile duct and were transplanted under the renal capsule in groups of 10–20 using standard procedures (Efrat, S. *ENDOCRINOLOGY* 128:897–901). At the indicated times following islet transplantation, the kidneys were removed, fixed in 4% buffered formaldehyde, dehydrated and embedded in paraffin. Five micrometer (5 µm) sections were collected on gelatinized slides, deparaffinized, rehydrated and stained with hematoxylin and eosin (H&E), or with guinea pig-anti-insulin or rabbit-anti-glucagon sera. The bound antibodies were visualized with horseradish peroxidase-conjugated second antibodies (Efrat, S. & Hanahan, D. *MOLECULAR & CELLULAR BIOLOGY* 7:192–198).

REVERSE TRANSCRIPTASE-POLYMERASE CHAIN REACTION (RT-PCR)

Total RNA was purified from the islets, digested with RNAse-free DNAse to remove any contaminating genomic DNA, and reverse transcribed using oligo dT priming (Fejer, G., et al., 1994, *J. VIROL.* 68:5871–5881). Each PCR reaction utilized 1% of the cDNA from one animal, 25 pmoles of each of the indicated primers (see FIG. 1), 1 unit of Taq polymerase, 250 µM of each dNTP, 2.5 mM $MgCl_2$, 50 mM KCl, 10 µg/ml gelatin and 10 mM Tris(pH 8.3). The sample was incubated for 10 min at 80° C., followed by 35 cycles for 1 min each at 94° C., 60° C. and 72° C. The amplified DNA was visualized by electrophoresis in a 1.2% agarose gel containing ethidium bromide.

DETECTION OF ADENOVIRUS PROTEINS IN CELLS CONTAINING THE E3 TRANSGENE

RIP-E3 mice were crossed with RIP-Tag mice (Hanahan, D., 1985, *NATURE* 315:115–122), and an insulinoma cell line (βTC-E3) was derived from a double transgenic mouse (Efrat, S., et al., 1988, *PNAS USA* 85:9037–9041). βTC-E3 cells ($3 \times 10^6$) were labelled with 1 $mCi^{35}$S-methionine for 5 hours in Dulbecco's modified Eagle's medium lacking methionine but containing 2% dialysed fetal bovine serum; these cells were harvested from the monolayers, washed free of radiolabel and lysed in a buffer containing NP40, in the presence of protease inhibitors (Fejer, G., et al., 1994, *J. VIROL.* 68:5871–5881). Control βTC6 cells (Knaack, D., et al., 1994, *DIABETES* (in press)) (without the E3 transgene) were similarly processed. L cells were infected with Ad2 (16,000 virions/cell), incubated with cytosine arabinoside (20 ug/ml), labelled from 16 to 21 hours after infection and processed in an identical manner to the βTC cells. Aliquots of the cell lysates ($2.2 \times 10^8$ cpm for the βTC; $1.5 \times 10^7$ cpm for Ad2-infected L cells) were immunoprecipitated with an anti-gp19 monoclonal antibody (Cox, J. H., et al., 1991, *J. EXP. MED.* 174:1629–1637) and protein A sepharose according to standard protocols. The immunoprecipitates were electrophoresed on 10% PAGE and visualized by autoradiography for 5 hours.

ADENOVIRUS E3 mRNAS ARE EXPRESSED IN THE ISLETS OF TRANSGENIC MICE

Figure 2:
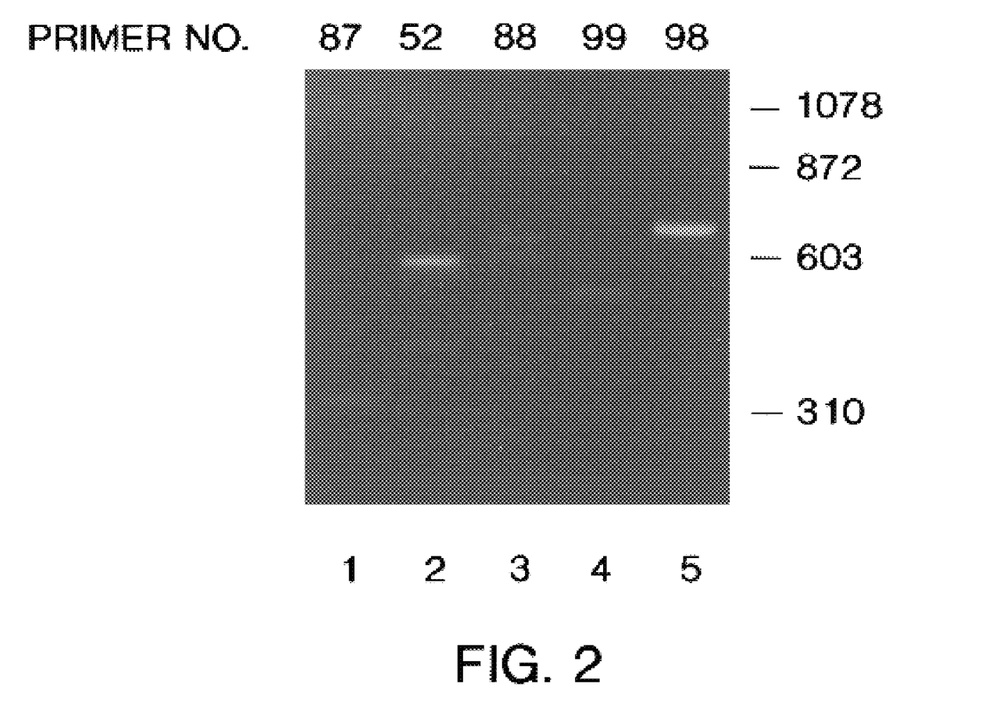
FIG. 2 depicts RT-PCR analysis of E3 mRNAs expressed in RIP-E3 islets. Transgenic islet cDNA was amplified with paired primers #53 and each of the indicated antisense primers as described in Materials and Methods. Size markers are in bp.

Transgenic mice were generated which express the E3 genes in β-cells under control of the RIP. The presence of the various E3 mRNAs in the transgenic mouse islets was determined by reverse transcriptase polymerase chain reaction (RT-PTC) analysis. Bands of appropriate size were detected using the common sense primer #53 in all reactions, together with the antisense primer #87, which detected all E3 MRNAs, #52 for gp19, #88 for the 11.6K, #99 for 10.4K, and #98 for the 14.7K (see FIG. 2). The upper band visualized in FIG. 2, lane 2, is of the size predicted for the gp19 primers. The origin of the lower band, which appeared intermittently as an RT-PCR product, has not been further characterized. The doublet of bands for the 11.6K (FIG. 2, lane 3) represents 2 alternate splice sites, one at nucleotide 1740 (FIG. 1), and another previously undetected at nucleotide 1792, which was confirmed by sequencing of the cDNA (data not shown).

GENERATION OF IMMORTALIZED ADENOVIRUS E3-CONTAINING β-CELLS FOR THE DETECTION OF EXPRESSED VIRAL PROTEINS

Figure 3:
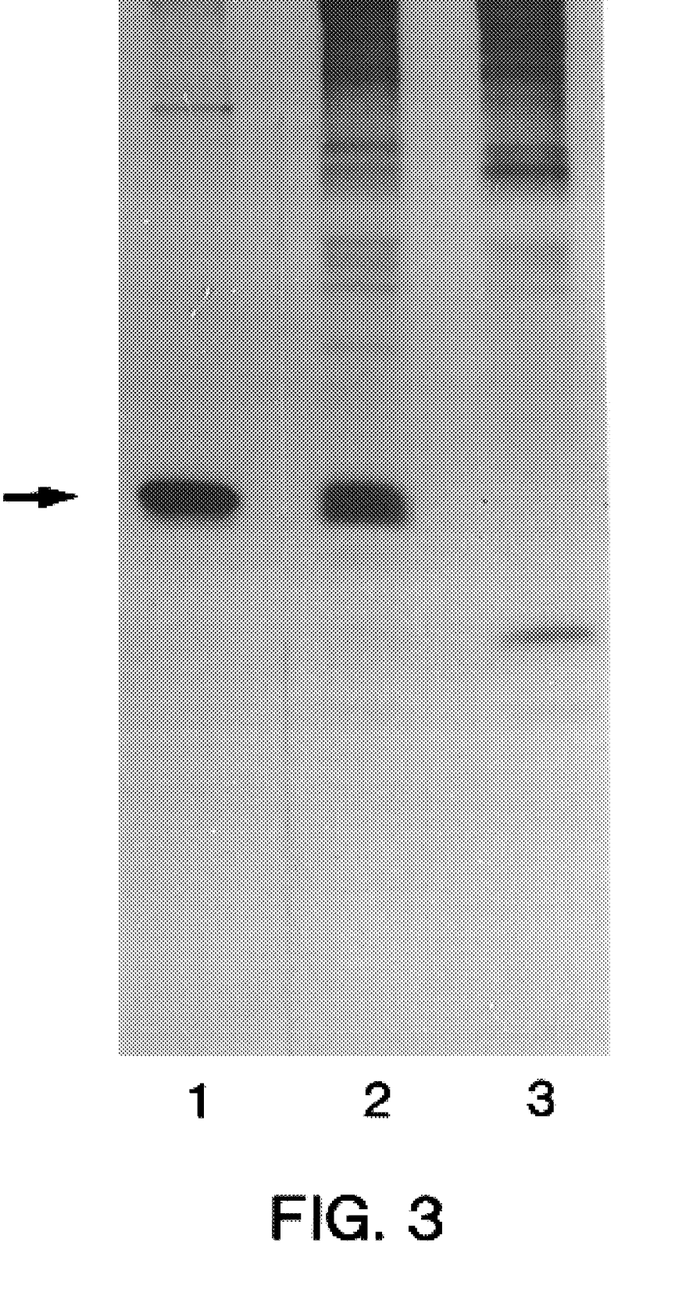
FIG. 3 depicts expression of the Ad2 gp19 in transgenic β cells. Cells were radiolabelled with $^{35}$S-methionine and gp19 was immunoprecipitated as described in Materials and Methods. Lane 1, Ad2-infected L cells; lane 2, βTC-E3 cells; lane 3, βTC6 cells. The arrow designates the gp19.

To obtain an abundant source of β-cells, the RIP-E3 mice were crossed with RIP-Tag mice, which express the SV40 T antigen (Tag) in β cells and develop insulinomas by 3 months of age (Hanahan, D., 1985, *NATURE* 315:115–122). Progeny expressing both transgenes were selected, and insulinomas that developed in the double-transgenic animals were cultured to derive β-cell lines. One of these lines, designated βTC-E3, was used to demonstrate the presence of the gp19 protein by radioactive labelling with $^{35}$S-methionine and immunoprecipitation with a gp19-specific monoclonal antibody (see FIG. 3). A radioactive band, which appeared on autoradiographs from extracts of β cells containing the E3 transgene (FIG. 3, lane 2), was not present in a control βcell line (βTC6) transformed with Tag but lacking the Ad E3 transgene (FIG. 3, lane 3). This band was also detected in extracts of Ad2-infected L cells (FIG. 3, lane 1). The lowest band in control lane 3 was present in immunoprecipitates of some preparations of pancreatic islets unrelated to the presence of the Ad2 E3 transgene.

RIP-E3 GENE PRODUCTS MEDIATE THE LONG-TERM SURVIVAL OF TRANSPLANTED ISLETS

Figure 4A:
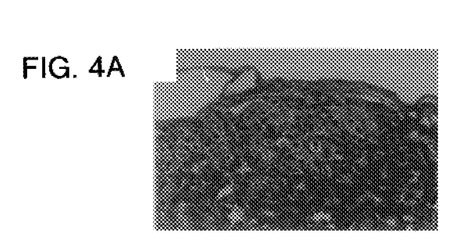
FIGS. 4A, 4B, 4C, 4D, 4E and 4F depicts the survival of Allogeneic RIP-E3 islet transplants. Donor RIP-E3 transgenic islets (H-2$^{b/d}$) transplanted for 91 days under the renal capsule of BALB/c (H-2$^d$) recipients were stained with hematoxylin and eosin (H&E) (FIG. 4A) or with antisera to insulin (FIG. 4C) or glucagon (FIG. 4E). Control B6D2/F1 (H-2$^{b/d}$) islets transplanted under the kidney capsule of BALB/c mice are shown at 14 days after transplantion (FIG. 4B), when infiltration with mononuclear cells was well developed only a few β cells that contained insulin could still be detected (FIG. 4D). In another section of kidney transplanted for 91 days with transgenic islets, a thin rim of mononuclear cells between the capsule and the islets was observed (FIG. 4F).

To assess the effect of the E3 proteins on allograft survival, RIP-E3 islets were transplanted under the renal capsule of allogeneic recipients. Donor islets from RIP-E3 [C57BL/6×BALB/c/F1 (H-$2^{b/d}$)] transgenic animals were transplanted into either BALB/c or C57BL/6 recipients. Normal C57BL/6×DBA/2/F1 [B6D2/F1 (H-$2^{b/d}$)] islets were transplanted into BALB/c or C57BL/6 recipients as controls. Islet survival was monitored by sacrificing the recipient mice and visualizing the donor islets under a dissecting microscope, followed by histologic and immunohistochemical analyses of kidney sections. Transgenic H-$2^{b/d}$ donor islets survived in the BALB/c mice for greater than 94 days, which was the last time point examined, whereas nontransgenic B6D2/F1 islets of the same H-2 genotype were rejected by all BALB/c recipients between 14–21 days following transplantation (see Table 1 and FIG. 4). In a subsequent experiment involving 5 animals examined between 14 to 28 days, nontransgenic C57BL/6× BALB/c/F1 islets were rejected by BALB/c recipients between 21–28 days post-transplantation. Histologic analysis of the RIP-E3 islets at 91 days following transplantion into BALB/c mice showed no inflammatory response within the islets (see FIG. 4A); however, a thin rim of mononuclear cells was observed near, but not infiltrating, the islets in some sections (see FIG. 4F). No inflammation was seen in the transgenic islets examined at 94 days, suggesting the sporadic rather than the progressive appearance of the peri-islet inflammatory response. The transplanted islets contained, in addition to β cells stained for insulin (see FIG. 4C), α cells that stained for glucagon (see FIG. 4E), and δ cells that stained for somatostatin (not shown).

Figure 4B:
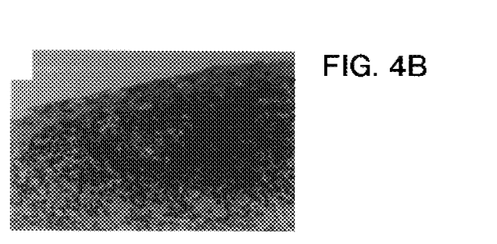
Figure 4C:
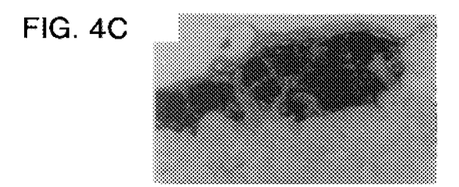
Figure 4D:
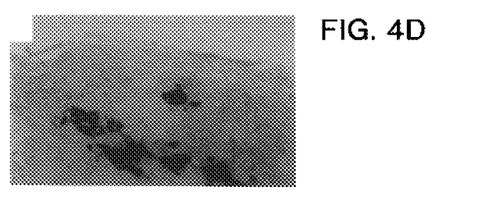
Figure 4E:
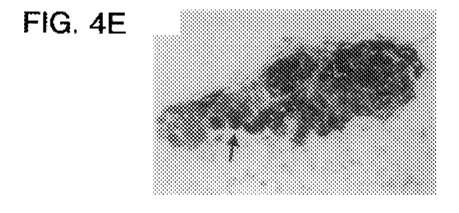
Figure 4F:
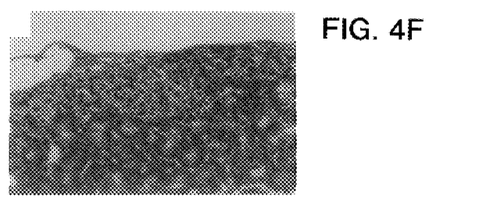

Analysis of the control nontransgenic B6D2/F1 islets transplanted into BALB/c recipients showed an intense mononuclear inflammatory response with islet infiltration at 14 days posttransplantation (see FIGS. 4B and 4D). In contrast to the transgenic donor islets that were accepted by BALB/c mice, islets from the same donor were rejected by C57BL/6 animals (Table 1), indicating that expression of the E3 transgenes protected against graft rejection in response to the $H-2^b$—but not the $H-2^d$—associated antigens presented by these donor cells.

ANOTHER EXAMPLE OF THE CONSTRUCTION OF AN ADENOVIRUS E3 REGION TRANSGENIC MOUSE

The adenovirus E3 Region, which encodes the gp19 protein and six other proteins was cloned and linked to the rat insulin promoter. Transgenic mice were constructed and a founder mice that genomic blots indicates has incorporated about 30–40 copies of the E3 transgene was selected. The presence of the major E3 region transcripts in the islet cells of the offspring of this mouse was confirmed by Reverse Transcriptase-PCR. The effects of the transgene were tested by transplantation of the islet cells from transgenic (B6× BALB/c)F$_1$ $H-2^{b/d}$ into the parental strains. Grafts placed under showed intact inlets without signs of rejection in necropsy observations made between days 25 and 94 after transplantation, the duration of the experiment. Inspection of a sixth animal hsowed no viable graft on day 91, which is compatible with a rejection or technical mishap. Grafts that were similarly implanted into C57B1/6 receipients were absent when necropsy was performed at between 25 and 32 days after engraftment, as is expected because of incomplete blockage of the $H-2^b$ expression of gp-19. Rawle, F. C., et al., 1989, J. IMMUNOL. 143:2037–37. These data indicate that the expression of gp19 is able to protect islet cells from immune rejection when transplanted between mice that differ at both MHC and background genetic loci.

CONSTRUCTION AND TESTING OF pHSVgp19

Figure 5:
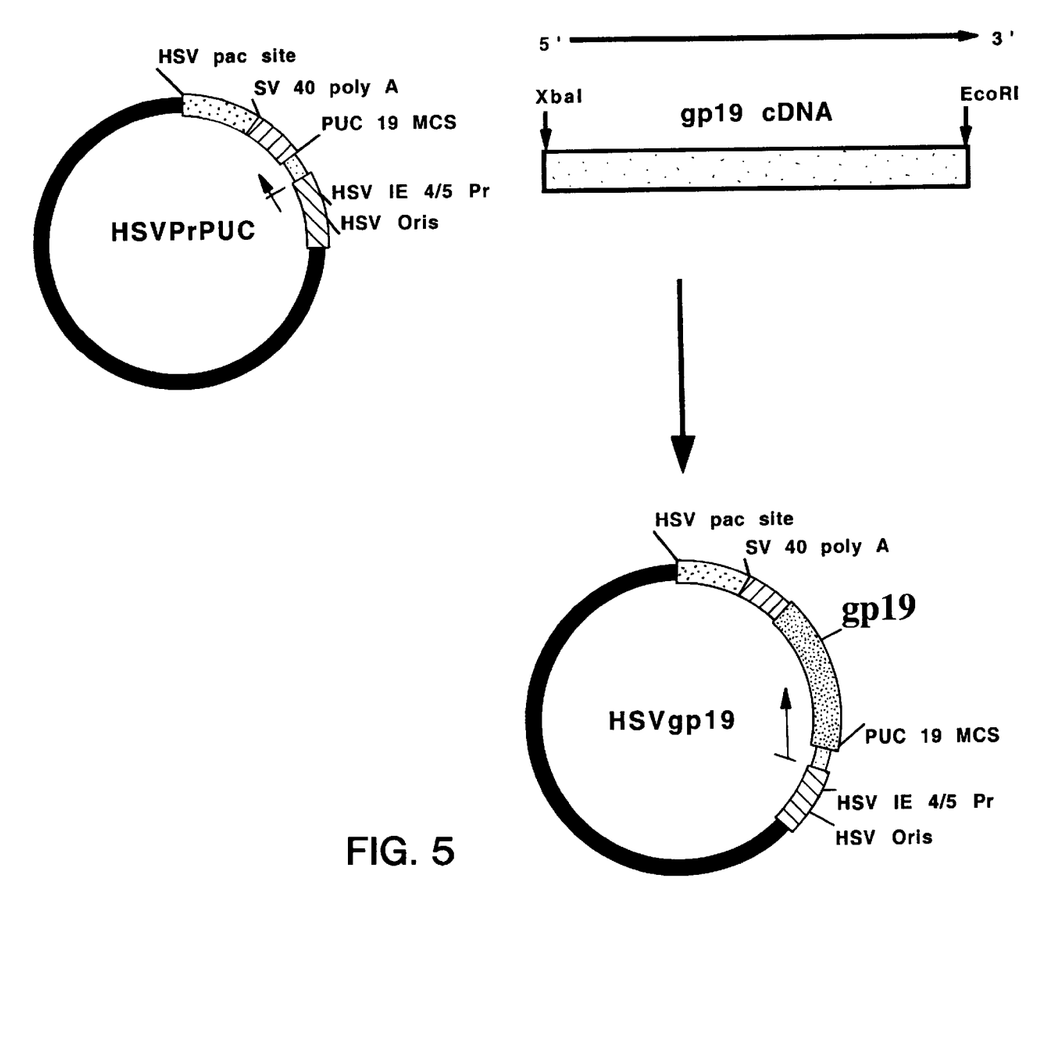
FIG. 5 depicts in diagrammatic form the construction of the pHSVgp19 vector from the gp19 cDNA insert and HSV prPUC.

The construction of the pHSVgp19 vector was carried out as follows: (see FIG. 5) the open reading frame (ORF) of the Ad 5 gene encoding gp19 was amplified with oligonucleotide primers (sense 5'TCGCTGGTCTAGACATCCAAGATGAGGTACAT3') and (antisense 5' CAAGCGAATTCTCAAGGCATTTTCTTTTCATCA3') by PCR using purified viral DNA as a template. The resulting PCR fragment was digested with restriction enzymes XbaI and EcoRI, cloned into pBluescript (Stratagene, Inc.), digested with the same enzymes and sequenced. The 505 bp fragment containing the gp19 ORF was excised from pBluescript with XbaI and EcoRI and cloned into the HSV amplicon vector pHSVPrPUC to make pHSVgp19. The plasmid pHSVPrPUC contains a HSV origin of DNA replication flanked by a truncated IE3 promoter fragment (truncated at −110) on one side and a complete IE4/5 promoter (IE3 truncated+ori$_s$+IE4/5; bases 131533 to 132558; a multiple cloning region from pUCI9; and SV40 polyadenylation site and HSV cleavage and packaging site (125771–126774). The sequence of HSV1 is available in Gen Bank Accession No. X14112, D00317, D00374 contributed by D. McGeoch.

Stocks of replication defective virus are prepared according to the teaching of WO 92/07945. The effects of pHSVgp19 are tested as follows. A human embryonic kidney cell line (293) is plated at about 5×10$^5$ per 35 mm diameter well and cultured for 24 hours at which time a concentrated stock of HSV amplicon pHSVgpI9 is added to the culture to achieve a multiplicity of infection of about 2. After 5 hours the cells are washed and continued in culture another 19 hours.

The cells are then trypsinized and removed from the culture well, washed and treated with 10 mg/ml papain in a 0.01 M pH 7.5 Tris buffered normal saline, 0.01 M cysteine for 45 min. The cells are washed and replated and cultured until control cultures which were papain treated but not transfected with pHSVgp19 have reexpressed MHC class I products. The cultures are then prepared for FACS analysis.

DEPOSIT OF MICROORGANISMS

The following were deposited with the American Type Culture Collection (ATCC), 12301 Parklawn Drive, Rockville, Maryland 20852 on ______________

| sample | containing | Accession No. |
|---|---|---|
| pHSVgp19 | gp19 HSV amplicon genome | ATCC _______ |
| pGX58 | Immediate Early Gene 3 | ATCC _______ |
| D30 EBA | helper HSV lacking IE3 gene | ATCC _______ |
| pGEM-ICP47 | Herpes Virus ICP-47 gene | ATCC _______ |

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

Various publications are references throughout this application. All such publications are hereby incorporated by reference into this application in their entirety.

TABLE 1

Survival of RIP-E3 Allogeneic Islet Transplants

| Donor islets | Recipient mouse | Time (days) after transplantation | |
|---|---|---|---|
| | | Grafts rejected+ | Grafts accepted* |
| RIP-E3 ($H-2^{b/d}$) | BALB/c ($H-2^d$) | 91** | 25, 32, 59,91,94 |
| RIP-E3 ($H-2^{b/d}$) | B6 ($H-2^b$) | 25,32,32,32,32 | |
| B6D2/F1 ($H-2^{b/d}$) | BALB/c ($H-2^d$) | 14,14,21,21,21 | |
| B6D2/F1 ($H-2^{b/d}$) | B6 ($H-2^b$) | 14++,21,21,21 | |

Islets were isolated from the pancreas and transplanted under the renal capsule as described in Materials and Methods as well as in the legend to FIG. 4. (+) No islets found at dissection; therefore, these represent maximum times to reject transplanted islets. (*) Islets intact at time of dissection; therefore, these numbers are minimal estimates of transgenic islet survival. (**) Another identically treated animal dissected on this day had normal islet transplants (see next column. (++) Animal dissected during active rejection (See FIGS. 4B&D). B6=C57BL/6; B6D2/F1=C57BL/6× DBA/2.

We claim:

1. A method for altering a pancreatic β-cell ex vivo comprising the step of introducing into said cell nucleic acid encoding the entire E3 region of an adenovirus under the control of a suitable promoter so that said nucleic acid encoding the entire E3 region is expressed in said cell in an amount sufficient to attenuate rejection of the altered cell in a non-immunosuppressed allogeneic recipient.

2. The method of claim 1, wherein the pancreatic β-cell is a human pancreatic β-cell.

3. A recombinant pancreatic β-cell suitable as an allograft, said cell being transfected with nucleic acid encoding the entire E3 region of an adenovirus under the control of a suitable promoter so that said nucleic acid encoding the entire E3 region is expressed in said cell in an amount sufficient to attenuate rejection of the cell in a non-immunosuppressed allogeneic recipient.

4. The pancreatic β-cell of claim 3, that is a human pancreatic β-cell.

* * * * *